United States Patent [19]

Rassman et al.

[11] Patent Number: 4,937,743

[45] Date of Patent: Jun. 26, 1990

[54] METHOD AND SYSTEM FOR SCHEDULING, MONITORING AND DYNAMICALLY MANAGING RESOURCES

[75] Inventors: William R. Rassman, Agoura, Calif.; Bradley M. Berman, Omaha, Nebr.; Scott Blau, Yonkers, N.Y.; Andrew Chiang, Fort Lee, N.J.

[73] Assignee: IntelliMED Corporation, Fort Lee, N.J.

[21] Appl. No.: 96,027

[22] Filed: Sep. 10, 1987

[51] Int. Cl.$^5$ .............................................. G06F 15/21
[52] U.S. Cl. .................................... 364/401; 364/518
[58] Field of Search ................. 364/401, 518; 434/108

[56] References Cited

U.S. PATENT DOCUMENTS

| | | | |
|---|---|---|---|
| 3,725,650 | 4/1973 | Gelder | 235/151.3 |
| 4,019,027 | 4/1977 | Kelly | 434/108 |
| 4,336,589 | 6/1982 | Smith et al. | 364/403 |
| 4,547,851 | 10/1985 | Kurland | 364/401 |
| 4,591,983 | 5/1986 | Bennett et al. | 364/403 |
| 4,646,238 | 2/1987 | Carlson, Jr. et al. | 364/403 |
| 4,700,318 | 10/1987 | Ockman | 364/518 |

OTHER PUBLICATIONS

"The Classifier", Mount Castor Industries, Inc., Abstract, citation from Microsearch File of Orbit, AN:-86-036077.
"Class Scheduling", CMA Micro Computer, Abstract, citation from Microsearch File of Orbit, AN: 86-035879.
"CSL Scheduling", Chancery Software Ltd, Abstract citation from Microsearch File of Orbit, AN: 87-040814.
Henry Fersko-Weiss, "Master Plan: Project Management Software", PC Magazine, Sep. 29, 1987, pp. 153-157.
Renouard, C. A., "A Computerized Inventory Model for Production Control", Control Engineering, Apr. 1971, pp. 61-64.
Andrew Layman, Time-Line, pp. 3-9, 14-27, 113-119, 124-127, 1984.

Primary Examiner—Jerry Smith
Assistant Examiner—Gail O. Hayes
Attorney, Agent, or Firm—Fitzpatrick, Cella, Harper & Scinto

[57] ABSTRACT

The invention relates to the method for the prospective scheduling, periodic monitoring and dynamic management of a plurality of interrelated and interdependent resources using a computer system. The method includes providing a data base containing information about the resources and graphically displaying utilization and availability of the resources as a function of time. Indicia can be made to appear on the display to provide visual identification of symbols as well as information about scheduling, status and conflicts involving the resources. In addition, access to the data base can be made available to provide a continuous update of the display so that the display of the resources is for the most recent data in the data base. Access to the data base can also permit the operator to call up a wide variety of information about the resources and can also be used to track events and procedures.

61 Claims, 9 Drawing Sheets

FIG. 8.

|  | Room 1 | Room 2 | Room 3 |
|---|---|---|---|
| 7:00 | Case abc | Case ghi | Case klm |
| 7:30 | Pt. Smith, Joe | Pt. Hill, Irma | |
| 8:00 | Dr. Jones, R. | Dr. Tom, Jack | Case mno |
| 8:30 | | Proc: D&C | Case prs |
| 9:00 | | Anes: General | |
| 9:30 | Case def | | Case tuv |
| 10:00 | | | |

FIG. 9.

|  | Rm 1 | Rm 2 | Rm 3 | Doc a | Mic x | Res y |
|---|---|---|---|---|---|---|
| 7:00 | Case abc | Case ghi | Case klm | Case klm | Case klm | Case xxxc |
| 7:15 | | | | | | |

Case # klm      June 2, 1987    Room 3   time 07:00

Patient: Jackson, Frederick M.
Address: 1102 First Ave, New York, New York
Diagnosis: Cataract
Procedure: Removal of Cataract   Duration 00:20
Surgeon: Leatherbarrow, Kenneth T.
Additional Diagnosis: ASHD
                    Pulmonary Emphysemia Time labels: 7:30, 7:45, 8:00, 8:15, 8:30, 8:45, 9:00, 9:15, 9:30, 9:45, 10:00

METHOD AND SYSTEM FOR SCHEDULING, MONITORING AND DYNAMICALLY MANAGING RESOURCES

FIELD OF INVENTION

The invention relates to a method for managing resources and particularly to the method and system for the prospective scheduling and real time dynamic management of a plurality of interdependent and interrelated resources using a computer system for communicating information.

BACKGROUND OF THE INVENTION

Many different fields require the management of resources in order to carry out programs and schedule activities effectively and efficiently. For example, the construction of a building requires scheduling the use of general and specialized personnel, of particular pieces of equipment and of delivery vehicles. In addition, a number of these resources may have to be shared with other construction projects at other sites. It also involves managing the rescheduling of the use of those resources as time passes and events unfold, often not in accordance with the original schedule.

Similarly, the efficient and effective use of surgical operating rooms in a hospital requires coordinating the use of numerous different resources, usually requiring collecting and gaining access to and then making use of information derived from many different sources. Some of the resources which must be managed and coordinated in a surgical suite or wing include the operating rooms, the surgeons, the anaesthesiologists, the residents, the nurses, the technicians, specialized pieces of equipment and the like.

In the last decade, there has been a significant increase in the use of computers and computer display systems for accessing and displaying data. For example, U.S. Pat. No. 3,725,650 discloses a method and arrangement for visually representing industrial management data. This patent teaches the use of a computer display for representing data in the form of bar-graphs or pie-graphs. The displays are for past and real time data and do not include projections into the future. In addition, each graph is independent of each other graph so that the impact of a change in one will not affect another. There is no suggestion in this patent that the method therein disclosed could be used for prospective or dynamic management of the utilization of resources.

U.S. Pat. No. 4,646,238 relates to a computerized system for planning the testing and grading of products as part of a manufacturing process. This patent does not disclose any system for prospectively scheduling the utilization of resources, nor does it disclose any method for monitoring actual utilization of resources, nor does it disclose a system where scheduling conflicts are noted.

U.S Pat. No. 4,547,851 relates to interactive communications systems used in restaurants for processing food orders by patrons and for making entertainment, like video games available to patrons. It does not relate to resource scheduling, either prospectively or dynamically.

U.S. Pat. No. 4,591,983 discloses a hierarchical knowledge system and does not appear to pertain at all to scheduling of interrelated and interdependent resources.

U.S. Pat. No. 4,336,589 discloses a method and system for monitoring and controlling the flow of articles in a warehouse. It is designed primarily to keep track of orders and of the articles ordered as they are taken from stock and prepared for shipment. There is no suggestion that such a system could be used for resource scheduling, management or monitoring.

Project planners which employ computers are also well known. Such project planners most commonly are task or activity focused. They are designed primarily for sequential scheduling of related tasks. For example, if a construction project must proceed through six phases, and phase 2 cannot begin until phase 1 is ⅔ complete, and phases 3, 4 and 6 each must await completion of the preceding phase, but phase 5 can begin simultaneously with phase 4, a project planner could be used to set up the schedule at the outset and to adjust that schedule to reflect slippages as they occur. Project planners, however, are not well equipped to manage the resources employed in the various activities or to alert the operators to the need to adjust the scheduled activities in response to other demands upon those resources.

The management of resources, utilization of which can change in time and can have complex interrelationships, can present serious problems to effective scheduling of the use of those resources and the tasks or activities in which they are employed. Inefficient and particularly incompatible solutions to these problems can be very costly in a manufacturing setting, in the construction of a building and elsewhere. Inappropriate solutions to such problems become far more serious when they involve medical facilities and the performance of surgery because they can then present life and death issues.

What is needed is an effective display of at least some of the available resources as a function of time associated with a data base of information relating to displayed resources and perhaps to others as well. In addition, such a system should, most advantageously, be capable of being accessed in order to produce additional displays relating to additional resources. In one of its more general forms, such a system should permit changing the time scale to accommodate widely diverse applications. Most desirably, it should also be able to display short range as well as long range projected (and/or historical) utilization without distorting relationships between displayed data when going from short to long range or vice versa.

Additionally, and, in some settings, most importantly, the system should be capable of showing interrelationships between resources so that changes in utilization of one or more resources, reveal the impact of those changes upon the availability and utilization of other resources as well as upon anticipated future utilization of the same resource and upon the activities in which they are employed.

SUMMARY OF THE INVENTION

The invention relates to a method for the dynamic management of a plurality of resources, preferably using a computer system. The method includes providing a data base that includes information about the available resources and graphically displaying anticipated and/or actual utilization of the resources as a function of time. Generally, the displays can be in the form of bar graphs, pie charts, line graphs or other geometric shapes. Various types of indicia may be employed to provide visual auditory or other sensory communication of information pertinent to the resources and/or the utilization thereof. "Scheduling indicia" may be used to indicate utilization (historical and/or prospective) of resources, "status indicia" may be employed to reflect current status of events and "conflict indicia" may be used to alert operators to scheduling conflicts. In one of its preferred configurations, the invention contemplates providing access to a data base to permit continuous updating of the information stored therein so that when resource utilization is displayed it reflects the most recent data in the data base.

In another embodiment, the method and system of this invention gives access to the data base in order to provide information, beyond that appearing on the display, relative to a selected resource. Provision can also be made for selectively changing the display in order to present data relating to different aspects of one or more resources.

Further, the invention contemplates the automatic adjustment of schedules as conflicts arise as well as the automatic communication of those adjustments. It also contemplates automatic notification to relevant personnel and automatic initiation of activities (cutting a purchase order, turning on a furnace etc.) and procedures upon reaching certain milestone points.

The system can also incorporate accountability means whereby it can be determined whether resources are being used properly and procedures are being followed in accordance with established rules. In addition, a record keeping function can be incorporated to document what resources were used, for what procedures, by whom and when.

Of course, not every application of this invention will necessarily incorporate all of the above features. It is anticipated that some applications will have need for only some of the features and other, more complex or more sophisticated or more automated applications will make use of more of the features contemplated by the instant invention.

BRIEF DESCRIPTION OF THE DRAWINGS

A description of the invention will be given in connection with the drawings which include:

FIG. 8 shows a reconfigured display of some of the information appearing on FIG. 1.

FIG. 9 shows a display wherein a pop-up window, overlayed upon the display of FIG. 1, shows information about case klm.

DISCUSSION OF THE INVENTION

Figure 1:
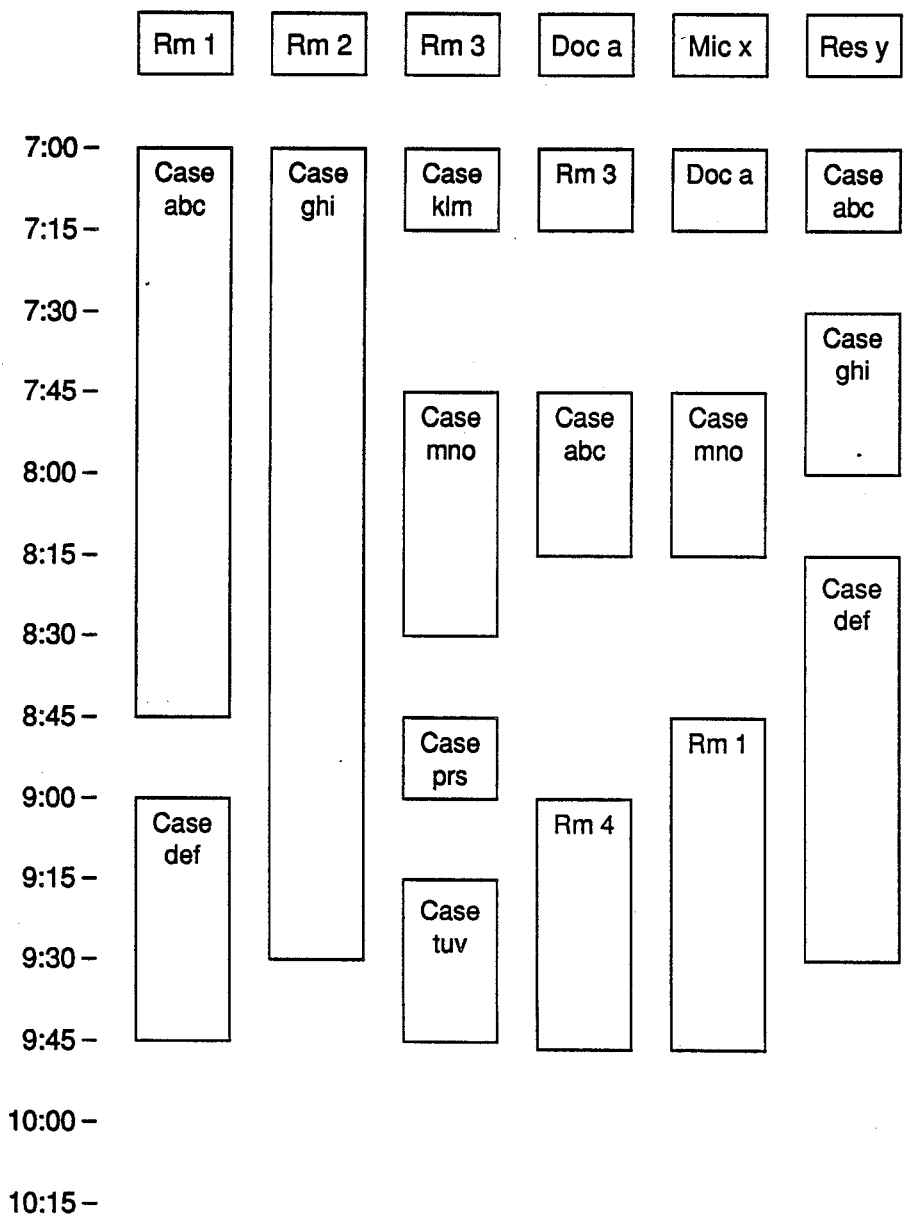
FIG. 1 shows a prospective display of scheduled resources in accordance with the invention.

The method according to the invention enables dynamic control of a complex project involving a plurality of resources which are interrelated and which can change with time. Preferably, the method utilizes a display system such as the type associated with a personal computer and a keyboard for selectively changing the display. In addition, a data base containing data relating to the resources can be made available. The data base can be updated from one or more real time sources and this in return can result in an update of the data being displayed. The keyboard can also be used to input data to the data base and to do prospective scheduling. The data preferably is displayed graphically as a function of time to portray the temporal relationships between various resources, activities and events.

Inputting, modifying, handling and accessing of the data can be carried out using known methods and techniques. Similarly, generating appropriate graphical displays can be done by using well known techniques.

There are numerous situations which can effectively be managed by the use of the instant invention. One such situation is monitoring and planning the use of the facilities and other resources available in the surgical suite of a hospital. Each operating room represents a resource and information can be provided in the data base about each operating room. For example, some operating rooms may be limited to ambulatory procedures, some may be specifically designed and equipped for open heart surgery, some may require only 15 minutes for clean up between procedures and others might need 20 minutes. Some specialized pieces of equipment may be limited to use in only some of the operating rooms. Some equipment may require long periods of sterilization between procedures, while others require none. Also, some resources may be unavailable because of construction, repair or maintenance activities. If the particular application calls for a rule-based system (as will be discussed below), the applicable rules would normally be in the knowledge or data base. Preferably, all such information would be included in a primary or semi permanent data base.

The primary data base could also include standard information about certain known activities or procedures. For example, it may include information like: an appendectomy should be scheduled to take 90 minutes, requires that medications A, B, C and D be available, that only operating rooms X, Y and Z are suitable for such a procedure and that only doctors J, K and L are authorized to perform such operations.

A supplemental, or transitory data base, preferably integrated with the primary data base, can also be employed to store information more frequently changed than the information in the primary data base. The transitory data base could include information about the planned utilization of a given resource on a particular day or at a particular time. Tasks or procedures waiting to be scheduled could also be in the transitory data base. It could also include relevant information about a particular patient (e.g., name, doctor, procedure to be performed, allergies) who is scheduled for surgery. If anything in the planned utilization is incompatible with information in either the primary or secondary data base, a conflict indicator can be made to appear on the display or on audible signal given. For example, if the procedure is schedule for a room in which construction is going on, a conflict indicator would be displayed. Similarly, if the patient is allergic to medication that is called for, a conflict indicator would alert the operator of the system to the problem.

Each surgical operating room has a planned use in time and the intended use may be associated with a particular patient, pieces of equipment and procedure, as well as key personnel who will be involved in performing the operation and the medication to be administered.

Each surgeon also represents a resource and the surgeon's prior commitments may be important for determining the availability of the surgeon for other surgical operations or in case of an emergency. In the same way, a patient can be regarded as a resource and the planned locations and activities of the patient can be displayed so that the patient can easily be located. Similarly, pieces of equipment and key personnel can be treated as resources. All this information would normally be put in the supplemental data base and would then be searched along with the primary data base, each time a resource is scheduled for use and each time a schedule is modified.

As can readily be appreciated, it is not unusual for the actual time taken to complete a particular procedure to vary from the scheduled or anticipated time. If the actual time exceeds the projected time, such information should be readily available in order to determine if alternate arrangements must be made. For example, such a deviation could affect subsequent scheduled use of the operating room. In addition, the extended involvement of the patient, the surgeon, key personnel and particular pieces of equipment could have an impact on other surgical procedures which have been planned for that surgeon, those personnel and those pieces of equipment. It could also affect other procedures that might have been scheduled for that patient.

As used herein, a "resource" in the hospital setting could be a room, a person, a piece of equipment, or the like. In other settings, "resources" could include containers, vehicles, supervisors, workers units of goods, blocks of time, dollars, aircraft, boarding gates, pilots and the like. Some resources may be reusable, others may be subject to depletion, and still others may be renewable. Generally, a resource has a known and/or anticipated availability and can be related to one or more other resources as a function of time or as a function of some other consumption, depletion or saturation. As those skilled in the art will readily appreciate, consumption, depletion, saturation and the like are analogous to time in that each can be used as a measuring yardstick. For example, a work day can be viewed as consisting of 32 fifteen minute blocks of time during which activities can be scheduled and resources used. Similarly, a reservoir of 2000 items may be viewed as consisting of 500 groups of 4, with various activities and resources scheduled for utilization as different groups of 4 are consumed. The term "time," as used herein, should be understood in its broadest sense and not limited to measurements based upon rotations of the earth.

The availability and utilization of resources can be displayed as a function of time by use of "scheduling indicia". Progress of a planned procedure can be monitored and displayed by use of "Status indicia." Incompatible scheduling of resources can be signalled by the displaying of "conflict indicia." Any of the several indicia, scheduling, status or conflict, described herein, can be displayed in a myriad of ways, including color changes, color bars, shadings, alphanumerics and the like, and combinations thereof. The several indicia can also be displayed by the use of highlighting, geometric symbols, flashing, and/or enhancements such as a brightened frame around data.

While the operator of the system can select certain resources for primary display purposes, the system monitors utilization, not only of the displayed primary resources but also of other or secondary resources which may or may not appear on the display, but which are used in conjunction with the displayed primary resources. To illustrate, the operator may choose to display "operating rooms" as the primary resources. One of those operating rooms, 0, however, may require surgeon S, anaesthesiologist A, heart/lung machine H and heart monitor M. Resources S, A, H and M may be referred to as secondary resources. If the procedure scheduled for room 0 takes longer than expected, the system will display conflicts, not only with respect to the primary resource, operating room 0, but also with respect to scheduled utilization of the secondary resources, surgeon S, anaesthesiologist A, heart/lung machine H and monitor M. The system can, of course, be so configured as to suppress one or more of these indicia.

In using the system of the instant invention, the operator collects information from various sources concerning needs or requests for use of the resources. In the context of a hospital surgical suite this might involve requests from surgeons for operating rooms, for pieces of equipment, perhaps for particular staff members and for other physicians, such as anaesthesiologist's. Each surgeon would identify the procedure to be performed, the anticipated time to complete the procedure, patient information and other relevant data. Other information might also be supplied, such as other commitments of involved personnel.

The operator loads this information into the data base in any conventional manner and then proceeds to schedule the various resources. If an attempt is made to set up a schedule that involves apparently inconsistent or incompatible use of a given resource, a conflict indicator would be displayed. Having thus been alerted, the operator would then either revise the proposed schedule or determine whether the conflict is real or only apparent.

To illustrate the difference between real and apparent conflicts, consider the situation of a surgeon employing a new procedure which only a few people have been trained to use. The new and unique aspect of the overall surgery may take only 30 minutes of an anticipated 3 hour surgery. The other steps to be performed, e.g., opening the patient in preparation for the critical procedure, stabilizing the patient on the heart/lung machine and closing the wound after the new procedure has been completed, could be performed by other surgeons. Nevertheless, since the operating room would normally be assigned to the primary surgeon for the entire 3 hour period, the system would display a conflict indicator if that primary surgeon were scheduled elsewhere during any part of those 3 hours. In the real world, however, that surgeon's personal presence might only be required for 30 minutes, thereby allowing him to discharge other duties during the remaining 2½ hours when the operating room is being used in his name.

Recognizing that some conflicts may be real and others only apparent, the system and method of the present invention can be made to recognize different kinds of conflicts, some which it "knows" are irreconcilable, some which it "knows" are susceptible of accommodation and some which it is unable to "recognize" as falling in either category. Each type of conflict could be indicated by its own unique conflict indicia. With that kind of information displayed, the operator can tell whether to reschedule resources immediately or whether to check further to see if a real conflict exits.

After collecting and usually, but not necessarily, after loading the relevant information into the data bank, the operator decides which resources are to be "primary" for display purposes and which are to be "secondary". In the hospital setting the operator may select "operating rooms" for display as the primary resources. Alternatively, "surgeons" or "heart/lung machines" or "CT scanners" or "nuclear magnetic imagers" etc. or some combination thereof might be chosen.

Assume, for illustration purposes, "operating rooms" is selected for display as the primary resources. Initially, the screen will display only the two axes—time (down the left margin), and operating rooms (across the top as column headings). Although at the outset the remainder of the display would normally be blank, it need not be. For example, for each unscheduled block of time the display can be made to show "open" or some equivalent designation. Also "repair" may be used to reflect that a particular room is not available for scheduling. Designations such as "repair," "construction" "sabatical" could be made to appear automatically as long as the requisite information has been stored in the data base.

The operator would then proceed to prepare a schedule, beginning with "Case abc" for operating room 1. The operator could schedule that case to begin at 7:00 a.m. and to end at 8:45 a.m. Or, if the information as to "Case abc" had already been loaded into the data base, once the starting time had been selected, an automatic search of the data base could cause the system to calculate and display the end point. In either case, a scheduling indicator would be displayed to reflect utilization of the primary resource, in this instance, "Rm 1". In FIG. 1, the vertical rectangle, labeled "Case abc" is the scheduling indicator. In similar fashion, the remaining operating rooms could be scheduled and scheduling indicia displayed. As long as nothing is planned for one of the primary resources at a particular time, the blank screen or "open" at that location would constitute the scheduling indicator.

During the scheduling of the primary resources, the system can be made to monitor conflicts in utilization involving primary as well as secondary resources. If such conflicts are detected, a conflict indicator will be displayed. The conflict could involve only primary resources, e.g. two procedures scheduled for the same operating room at the same time. In that event, the operator would be able to detect the nature of the conflict on the display. However, the conflict could involve secondary resources, some of which may not appear on the display. In that event, the operator would be alerted to look for the conflict among the secondary resources. Alternatively, by use of color, shading, shape positioning or the like, the conflict indicia itself can identify the secondary resource which is the source of conflict.

On the display, a scheduling indicator showing planned or actual use of a particular primary resource during a given block of time can be referred to as a "cell". On FIG. 1 the rectangle showing that "Case abc" is scheduled for Room 1 from 7:00 to 8:45 a.m. would be a "cell". Each cell could be given a title which could be made to appear above the cell or within its confines. Space permitting, a cell could also be made to have several pieces of data relating to secondary resources displayed therein. For example, within the cell that represents "Case abc" the name of the surgeon or the type of equipment being employed could be displayed.

In the event it is decided to display secondary resources within cells, such secondary resource displays could be used to indicate conflicts. For example, if Doctor S were scheduled simultaneously in two operating rooms, the display of Doctor S as a secondary resource in either or both of those cells could be made to flash. Such flashing would, in that embodiment, constitute the conflict indicia.

The display of secondary resources could also be employed to make additional options available. For example, instead of having to go through a menu, simply by moving the cursor to one of those displayed secondary resources, the system could be made to display a window with that secondary resource s schedule or other information about that secondary resource. Such a window is shown in FIG. 9.

Thus, the system need not be menu driven. The use of shortcuts, such as displays of secondary resources within cells, may avoid the use of menus. However, in the more complex and/or more sophisticated applications of the instant invention, it is unlikely that sufficient short-cuts can effectively be used so as to avoid all use of menus.

Figure 4:
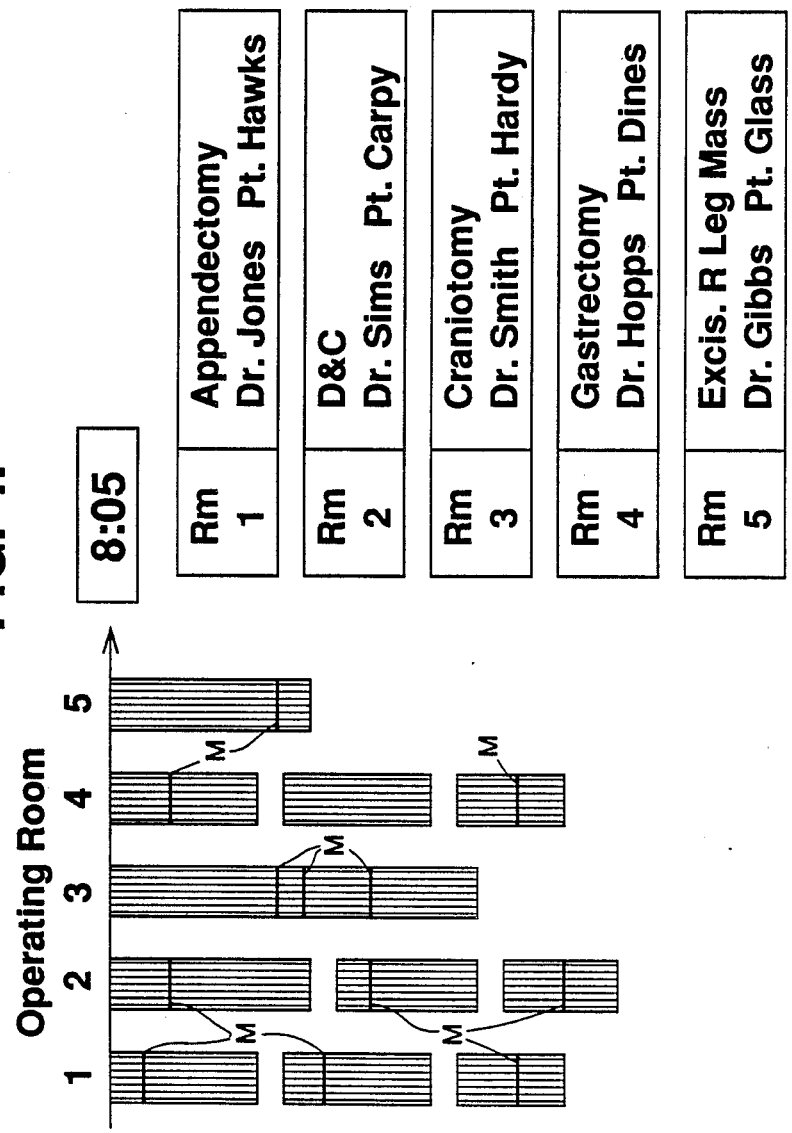
FIG. 4 shows an alternative method for graphically displaying scheduling information while simultaneously displaying in textual form, information about the scheduled resources.
Figure 5:
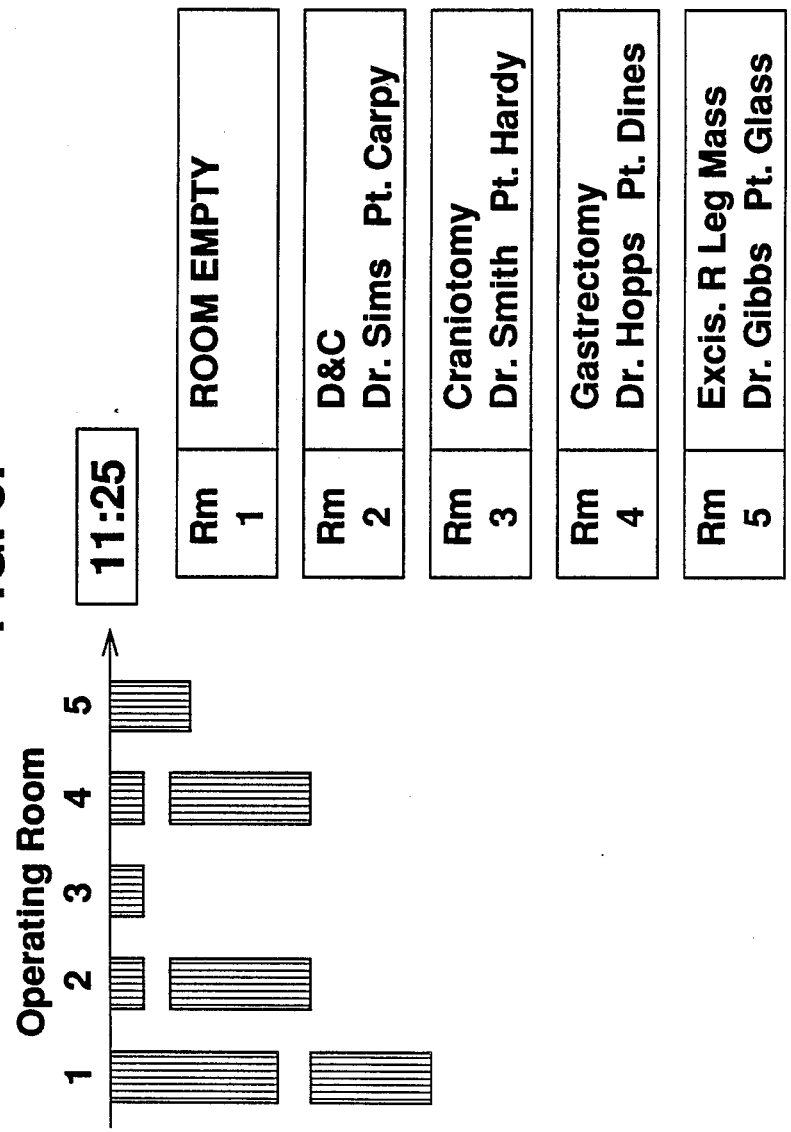
FIG. 5 shows the display of FIG. 4 at a later point in time.

In the displays illustrated in FIGS. 1 through 3 and 6 through 8, along the Y axis time is shown running from top to bottom, and along the X axis the primary resources are shown. As will readily be understood, which resources to display, and along which axis is a matter of choice and convenience. Similarly, the time intervals can be selected to match the needs of the application. Moreover, as illustrated in FIGS. 4 and 5 those time intervals need not even be displayed.

Turning now to FIG. 1, the display depicts a mixture of resources and their availability in time. The resources are labeled across the top using abbreviations in which "Rm" is room, "Doc" refers to a medical surgeon, "Mic" refers to a particular type of apparatus, namely a microscope and "Res" refers to some other piece of equipment.

The time is shown at the left in FIG. 1, starting with 07:00, based on a 24-hour clock. It is usually most convenient to have all of the primary resources in a display of the same type, such as rooms. However, such uniformity is not essential. As can be seen, the primary resources selected for display in FIG. 1 are of three different types. The primary resources in the first three columns, "Rm 1", "Rm 2", and "Rm 3", are of one type, but the the primary resources of the last three columns, are of two other types. The primary resource of column 4 is a surgeon and the primary resources of columns 5 and 6 are pieces of equipment.

In FIG. 1, "Rm 1" can be taken to refer to a surgical operating room. At 07:00 in the morning "Case abc" is scheduled to occupy "Rm 1" until 08:45. Thereafter, "Case def" will be in "Rm 1" from 9:00 until 09:45.

Rm 2 has "Case ghi" from 07:00 to 09:,30. Rm 3 has "Case klm" from 07:00 to 07:15 which is followed by "Case mno" from 07:45 to 08:30. "Case prs" follows from 08:45 to 09:00 and then "Case tuv" from 09:15 to 09:45.

While there may be many surgeons involved, only the activities of the surgeon "Doc a" are shown. "Doc a" will be in Rm 3 from 7:00 to 7:15, involved in "Case abc" from 7:45 to 8:15 and in Rm 4 (not displayed) from 9:00 to 9:45. "Mic x" will be used by "Doc a" from 7:00 to 7:15, will be used for "Case mno" from 7:45 to 8:15 and will be in room 1 from 8:45 to 9:45. Also, the resource "Res y" will be used for "Case abc" from 7:00 to 7:15 (even though "Case abc" will continue long after 7:15) and will then be moved for use in "Case ghi" (already in progress) from 7:30 to 8:00. Resource "Res y" is then shown as being assigned to "Case def" from 8:15 to 9:30. Although "Case def" is not scheduled to begin until 9:00, keeping "Res y" available for that case from 8:15 does not necessarily represent a conflict, although it may represent a waste of a valuable asset. Depending upon the needs of the particular application, such scheduling of "Res y" could, but need not, trigger the display of a conflict indicator.

In FIG. 1, "Case abc" is scheduled from 7:00 to 8:45. "Doc a" is scheduled to be involved in that case, but only from 7:45 to 8:15. He is also scheduled for "Rm 3" ("Case klm") from 7:00 to 7:15. If "Case abc" is Doc a's case, then when the operator tried to schedule him for Rm 3 ("Case klm") from 7:00 to 7:15 a conflict indicator would have been displayed. The operator would then have checked, determined that Doc a was needed in Rm 1 ("Case abc") only from 7:45 to 8:15 and then overridden or suppressed the conflict indicator.

The display in FIG. 1 represents the results of a prospective scheduling of activities and has been presented for a predetermined time period. Revising the time scale (from 15 minute to 30 minute intervals, for example) will allow the operator to see further into the future but will result in the size of the scheduling indicia to be physically reduced. The distances between cells under each resource will also shrink so that resolution of adjacent cases in time may not be discernible. Such shrinking of the time scale will also permit less information, for example, about secondary resources, to be displayed within each cell.

Time scale compression may also trigger conflict indicia. For example, if the scale of FIG. 1 were changed from 15 minute intervals to one hour intervals, conflict indicia would be displayed between several of the cells, including "Case abc" and "Case def" in Rm. 1. Each cell would be occupying a portion of the time block 8:00 to 9:00.

The use of conflict as well as status indicia to communicate data permits communication of multi-dimensional information on a two dimensional display. Some of the data which cause the display of conflict or status indicia may be drawn from the semi-permanent data base, some may be from the transitory data base and some may be from current or real time inputs.

In a hospital surgical wing application, as well as in many other applications to which the instant invention can be put, inclusion of an internal real-time clock would be quite advantageous. For example, such a clock could be used to tell the operator which resources are in use and which ones are available at the time of viewing. It could also enable the viewer to determine where a particular resource, such as "Doc a" is at the present time. In addition, the inclusion of a real-time clock can enable automatic display of conflict indicia.

Figure 1A:
FIG. 1A shows one of the cells from FIG. 1 after the first milestone has been completed.
Figure 1B:
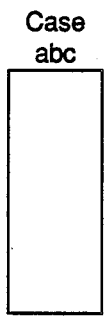
FIG. 1B shows one of the cells of FIG. 1 with the identifying label having been moved to above the cell to denote that the patient is in the room.
Figure 1C:
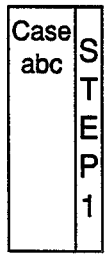
FIG. 1C shows the same information as in FIG. 1A, but using a different means to indicate completion of milestone 1.
Figure 1D:
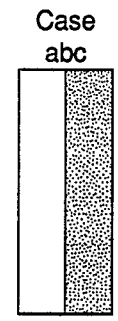
FIG. 1D shows the same cell as FIG. 1A, but at a later point in time, after the second milestone has been passed.
Figure 1E:
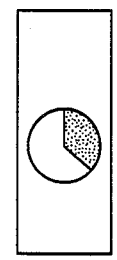
FIG. 1E shows a cell in which a circle or clock face is used to display status indicia.

If timely information is available, status indicia can be used to monitor and display progress of a procedure. The entry of the patient into the operating room could be signalled by use of the identifying label. "Case abc" could be blue before the patient enters, orange as long as the patient is in the room and red after the patient has left. Alternatively, the label could be moved from within the cell to a site just above it to signify that the patient is in the room (FIG. 1B). Other status indicia could be used to monitor progress of the surgery. One way to do that would be to have the cell representing the time the patient is in the operating room changed progressively as the surgery proceeds toward completion. For example, initially the cell can be changed so that one-quarter of it along its time length is in a contrasting color or distinctive pattern (FIG. 1A) to indicate that step 1 has been completed. Another way would be to use alphanumerics, such as "Step 1" in a column occupying the first quarter of the scheduling indicator cell (FIG. 1C). If the label is used to signify entry of the patient, the first column within the cell would be used to indicate completion of step 1 (FIG. 1C). Status indicia might also take the form of a clock face, part of which is shaded or colored as the procedure progresses or as time passes (FIG 1E). Moreover, a combination of such indicia could also be used.

When a second milestone or significant stage has been reached, a second status indicator could be displayed. As an example, a second column, ¼ the width of the cell, could be changed to a contrasting color (FIG. ID). Additional indicia, for example, additional columns within the cell, could be used to represent other milestones or significant stages during the surgery.

The method of the instant invention, when a real-time clock is incorporated, can be made to display status indicia automatically. To illustrate, "Case abc" (FIG. 1) might involve four major stages. Assume that stage 1 is expected to take twenty minutes, stage 2 thirty minutes, stage 3 forty minutes and stage 4 fifteen minutes. Means, for example, a signal button, can be provided in the operating room to indicate when each stage has been completed. If that button is depressed on or before 7:20 a.m., a status indicator in the form of a vertical bar within cell "Case abc" and occupying ¼ of that cell, can be made to appear (FIG. 1A). However, if the real-time clock reaches 7:21 before the signal button is depressed, that status indicator can be made automatically to begin flashing and to continue flashing until the indicator button is depressed. Such flashing of a status indicator can alert the operator to the fact that the procedure is taking longer than anticipated. With such information in hand, the need for rescheduling can be anticipated before the situation becomes critical.

The real-time clock could also be used for automatic display of conflict indicia. If the signal button in Rm 3 has not been used to signify that "Doc a" has completed his task before 7:45 , a conflict indicator can be made to appear because Doc a is scheduled to be in Rm 1 working on Case abc at that time.

Status indicia may, but need not be communicated according to a predetermined sequence. In some procedures sequencing may not be important with respect to some or all of the stages of the procedure. When sequencing is imperative, the method and system of the present invention can be made to operate in a programmed mode. Each time a milestone is reached, all that the operator need do is depress a button. Each button press signals the reaching of the next milestone in a predetermined sequence.

In other applications, however, a manual mode might be more suitable. In the manual mode, the operator, by movement of the cursor or some other mechanism, first identifies the stage or milestone and then signals its completion. Thus, the operator could, in the manual mode, signal completion of stage 3 before stage 2.

Hybrids of the two modes may also be employed. Thus, even in the manual mode, predetermined sequences or rules may be established. For example, it may be necessary that step 3 be completed before step 4 is begun, but steps 1, 2 and 5 may proceed without regard to the timing of steps 3 and 4. Conflict indicia can be made to signal the violation of any sequence rules.

As can be appreciated, many installations are likely to want the flexibility of selecting either the programmed mode, the manual mode or the hybrid mode. The present invention readily accommodates such flexibility.

Frequently it is important that a record be kept of what happened and when. This can be accomplished according to the instant invention simply by recording (e.g. in the memory or on a printout) the time when each milestone is reached. Normally, a real time record, using the real-time clock, would be made each time a milestone signal is sent. However, often, contemporoueous signalling is impossible. For example, during surgery, no one may be free to depress the signal button at the time a milestone is reached. Therefore, the present invention also contemplates means for manual entry of the time when an event occurred. It also contemplates use of appropriate indicia, usually on the historical record, of whether the time recorded was real-time or was manually entered.

The historical record also provides for accountability. From that record it can readily be determined what sequence was followed, when each milestone was reached and which resources were involved. to reschedule the resources involved in the second tier conflict and only if no conflicts result from that second rescheduling, to proceed to reschedule at both the first and second tiers. Otherwise, the rule would require abandoning the effort to reschedule.

The instant invention also contemplates the use of status indicia to predict unanticipated availability of resources. For example, if stage 2 in "Case abc," not expected to be finished until 7:50, has been completed before 7:40, the status indicator bar (FIG. 1A) can be displayed in a different contrasting color. The appearance of such a color bar on the display would alert the operator to anticipate availability of operating room 1 (and the other resources involved in "Case abc") earlier than originally expected.

Figure 2:
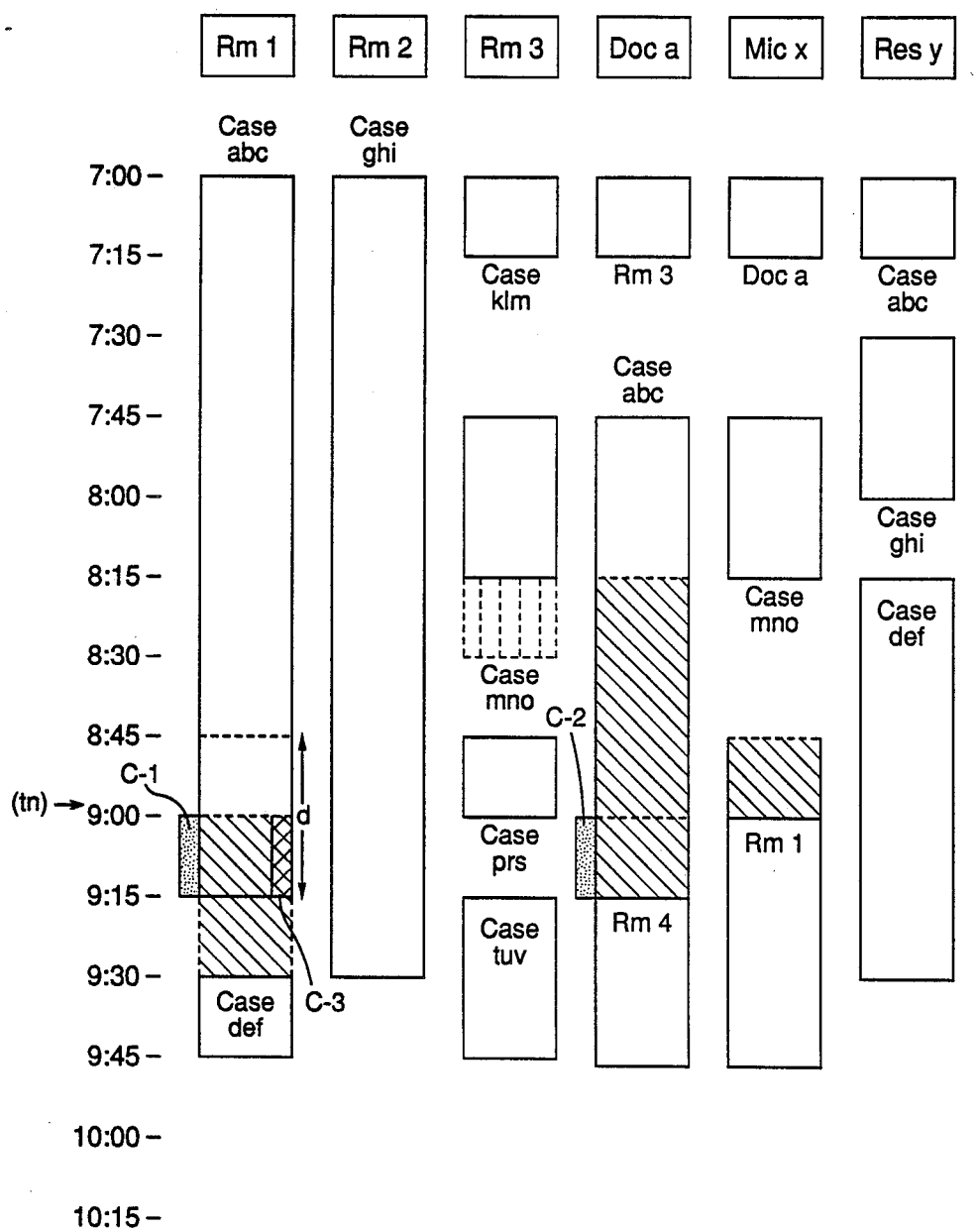
FIG. 2 shows the schedule of FIG. 1 as a dynamic display, modified in accordance with the present invention by events as they have occurred.

FIG. 2 represents a dynamic display of information based on real-time information, as contrasted with the static prospective information that is reflected in FIG 1. On FIG. 2, the time now is indicated by "(tn)" and an arrow.

FIG. 2 shows a conflict between "Case abc" and "Case def" for surgical operating room 1, as denoted by conflict indicator C-1. This conflict could have arisen as a result of the operator, reacting to status indicia, revising the anticipated completion time of "Case abc." Alternatively, it may have been triggered by the passage of time (as indicated by the real-time clock) beyond 8:45 without a signal having been received that "Case abc" has been completed.

It should be noted that the revision of the scheduled completion of "Case abc" also causes a conflict in the schedule of "Doc a" who is supposed to be in "Rm 4" at 9:00. Conflict indicator C-2 reflects that conflict.

The system can also be made to take certain actions automatically. For example, if a piece of equipment must be warmed up for a predetermined period of time before use, the method of the instant invention would encompass having the system energize that piece of equipment when a particular milestone in the procedure has been completed. Similarly, in an industrial setting, the system could automatically cut purchase orders or open molds when certain predetermined milestones are reached.

The method of this invention also contemplates a rule based system wherein the detection of certain conflict indicia would cause automatic rescheduling of some resources. To illustrate, assume that in FIG. 1, there must be 15 minutes between completing Case abc and beginning Case def. If a signal has not been sent by 8:50 that Case abc is over, a rule could be established that would automatically reschedule Case def to begin at 9:15. The rule could also require checking the schedules of all the resources involved in Case def before rescheduling.

If, upon checking those Case def-related schedules no new conflicts are detected, the rescheduling would be done and notice of the change communicated automatically to the people affected. This could be done, for example, by having the system call the office of the surgeon scheduled to do Case def and, by use of a voice synthesizer, report the new schedule.

If the rescheduling of Case def is found to provoke other conflicts, the system could be designed so as not to do the rescheduling, but instead merely to give notice of the first conflict. That notice could be by means of a visual display, by the sounding of a distinctive note or the like. Another possibility would be to have the system try:

Ideally, conflict indicia would be displayed regardless of which resource or resources are involved. For example, even if the unexpected delay in completing "Case abc" did not cause a conflict in use of Room 1, it may have caused a conflict in the schedule of the anaesthesiologist involved in that case. If the anaesthesiologist's schedule had been placed in the data base, a search of the data base in response to rescheduling of the completion of "Case abc" would reveal that the anaesthesiologist's extended involvement in "Case abc" conflicts with his other obligations. As a result, yet another conflict indicator C-3 would be displayed. Conflict indicator C-3 could be non-specific, in that it would merely reflect the existence of a conflict but not identify the source. Conflict indicia C 1 and C 2, on the other hand signify not only the existence of a conflict but also identify one or more of the resources involved. Alternatively, C-3 could be made specific by use of color, position, shape etc.

It should be noted that identifiers "Case abc" and "Case ghi" under rooms 1 and 2 have been moved from within the cells to above them to indicate that those cases are currently proceeding in their respective operating rooms. The identifier "Case abc" under "Doc a" has also been moved to above the cell to reflect that Doc a is currently involved in that case.

Under Rm. 1 on FIG. 2, it can be seen that the scheduled completion time has been changed from 8:45 to 9:15, representing a delay (d) of 30 minutes. The cross-hatching under Rm. 1 shows that Case def, originally scheduled to begin at 9:00, will not begin until 9:30.

The locations of the identifiers under Rm. 3 immediately reveal that Cases klm, mno and prs have been completed and that Case tuv has not yet begun. It can also be seen that Case mno was originally scheduled to end at 8:15 but did not actually end until 8:30.

Still on FIG. 2, under "Doc. a", it can be seen that his involvement in Case abc did not end at 8:15 as planned, but is still in progress at the current time and is now scheduled to end at 9:15.

Finally, it can be seen that Mic. X, initially scheduled to be moved into Rm. 1 at 8:45, perhaps to permit set-up and calibration in advance of Case def, has not yet been moved in, and is not scheduled for that move until 9:15.

Figure 3:
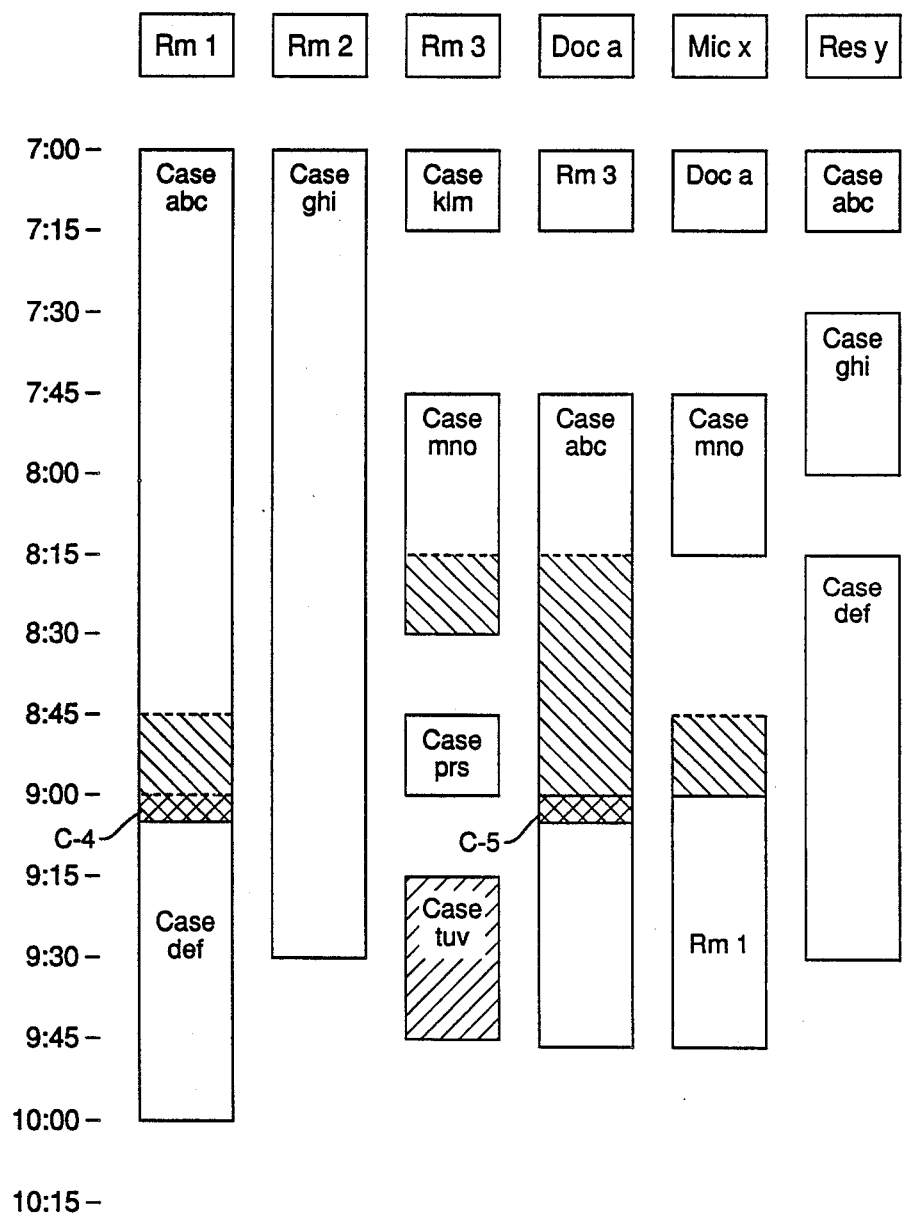
FIG. 3 shows the schedule of FIG. 1 after completion. It is an historical record generated in accordance with the present invention, showing not only what took place, but also how reality varied from projected utilization.

FIG. 3 is an historical display of how the primary resources were actually used relative to the schedule shown in FIG. 1. In FIG. 3, it can be seen that "Case abc" which had been planned to be completed at 08:45 (dashed line in "Case abc" cell), was not completed until about 09:05 and "Case def" started immediately thereafter. Conflict indicator C-4 (double cross-hatching) shows that "Case def" did not begin at the time anticipated. Similarly, conflict indicia show that "Doc a" did not begin the procedure in Rm 4 until 9:05 (C-5) because he was delayed by Case abc.

In the embodiment of FIG. 3, indicia in the form of single cross-hatching, are used to show changes that were made from the prospective schedule. The opposite direction cross-hatching of the Case tuv cell denotes a cancelled procedure.

It should be noted that neither FIG. 1 nor FIG. 3 shows a current time indicator. In order to keep the two types of displays from being confused, some notation would normally be used to differentiate one from the other. One such method would be to use one background color for prospective displays and a contrasting background color for historical displays. Such use of contrasting colors could also make superflous a separate current time flag. On the dynamic display, the passage of time could be shown by having the interface line between the two colors move inexorably downward.

The display of FIG. 2 contemplates showing time passing by having the time arrow (tn) move down the screen, with the cells remain stationary. As those skilled in the art will readily appreciate, the time line can be held stationary while the cells move. One such display is reflected on the left half of FIG. 4. As time passes, the digital clock changes and the cells index upwardly.

FIG. 4 also shows how, in accordance with the instant invention, a graphical display may be combined with and supplemented by a real time textual display. As one cell passes off the screen, the textual display showing current utilization of that resource would automatically change to reflect the new circumstance.

FIG. 4 shows the situation at 8:05. FIG. 5 shows the situation with respect to the same operating rooms at 11:25. It should be noted that the time relationships between cells have changed between 8:05 (FIG. 4) and 11:25 (FIG. 5). This has occurred because embedded in the cells in this embodiment are milestone markers (M). The cells stop at each of these milestone markers until indication is received that the milestone has in fact been reached. The cell then resumes indexing upwardly. In this embodiment, the combination of milestone markers and cell movements constitute the status indicia.

Figure 6:
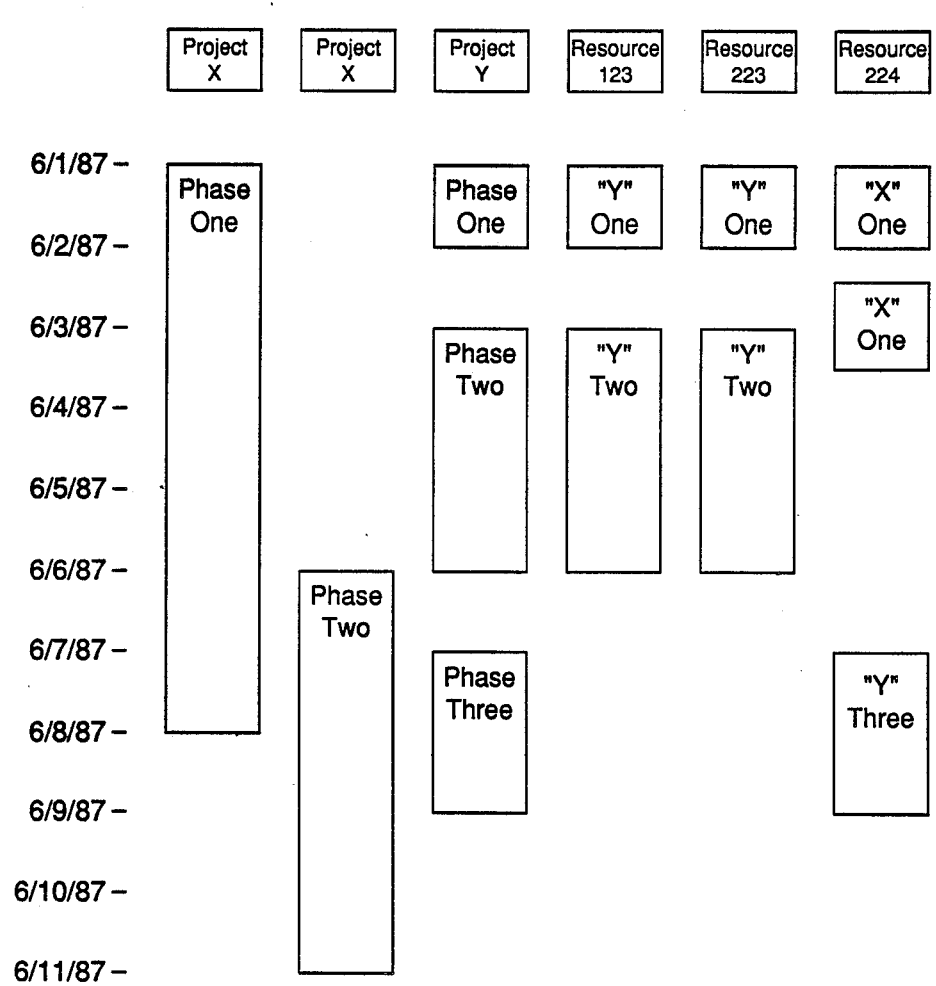
FIG. 6 shows a display of a prospective schedule of industrial projects in accordance with the invention.

FIG. 6 shows a display of a prospective schedule for the beginning of the month of June 1987 for Projects X and Y and Resources 123, 223 and 224. Project X has two phases which can be partially overlapping. Project Y has three phases none of which can overlap. Resources 123, and 223 are used in phases 1 and 2 of Project Y. Resource 224 is used twice during phase 1 of Project X and in phase 3 of Project Y.

Figure 7:
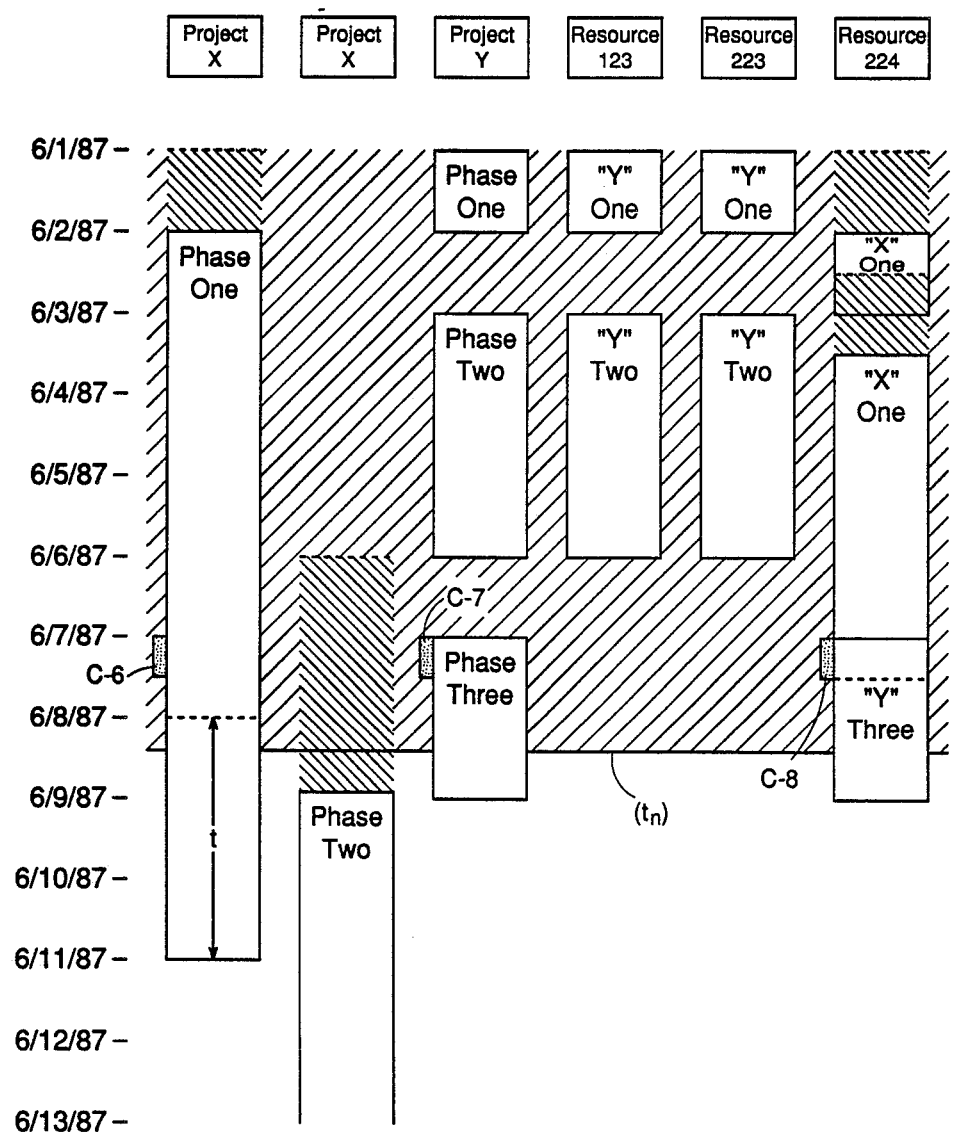
FIG. 7 shows an dynamic display of the schedule of FIG. 6, modified to take into account some events as they have occurred.

FIG. 7 shows the dynamic or actual events as of June 8, 1987 with respect to the schedule shown in FIG. 6. Phase of Project X did not begin on time and ended late. The late ending is indicated by arrow t in the "phase one" cell. That delay has caused a conflict to arise because Resource 224 cannot be used concurrently in phase 1 of Project X and phase 3 of Project Y. This conflict is indicated by indicia C-6, C-7 and C-8. The time is indicated by a screen background color change. The interface between the two colors is the current time (t).

Although Project X and Resource 224 used in Project X have been rescheduled on FIG. 7, Project Y phase three and the use of Resource 224 in "Y" three have not yet been rescheduled.

While some overlap between phases one and two of Project X was anticipated, the delay in completion of phase one resulted in too great an overlap, and the start of phase two had to be delayed as a result. This is indicated by shading in the Project X, phase two cell.

FIG. 8 shows a display relating to FIG. 1 which has been reconfigured to include additional information about some of the cells.

As discussed above, the method and system of the instant invention may be menu driven. The nature of the menus and submenus, the information to which they permit access and the other functions they make available will vary depending upon the application. Some menus can be used merely to call up information from the data base. Other menus can be used to modify the display format. How such menus can be used and the kinds of menus which can be made available are as varied as the applications to which the invention may be applied and the creativity of those who use the invention.

The conventional use of pop up windows allows additional information to be displayed beyond that which can conveniently be placed on a graphical display. In FIG. 9 a pop up window has been called up in order to view detailed information concerning a particular case.

The display can also be used to trace the location of a specific physician or patient. The data base in a hospital system could also allow the display of the availability of other resources, unrelated to the surgical suite. For example, a hospital system could be designed to identify the present and future occupants of rooms so that individuals could be easily located and timely information retrieved as to availability of rooms.

Although it is anticipated that, at least in the early applications of the instant invention, inputting of information will normally be through key boards and/or signal switches, it should be understood that the invention is not limited to use of such devices. Depending upon the particular application, telephone, radio, microwave, infrared and other devices and methods of transmitting signals could be used. In an industrial setting where dynamic scheduling depends upon personnel in the field arriving and departing from a myriad of different locations, telephones or "beepers" could be used to input current information. Similarly, conflict indicia or rescheduling information could automatically be communicated to field personnel by means of "beepers" or other such devices.

While it is believed that a cathode ray tube display is most suitable for use in practicing the instant invention, the term "display" has been used herein much more generically. Depending upon the particular application, hard copy, e.g., a paper print-out, might be an acceptable display. Similarly, an array of incandescent bulbs might be adequate. Other, more or less sophisticated displays could also be employed.

Finally, the above-described embodiments of the invention are intended to be illustrative only. Numerous alternative embodiments may be devised by those skilled in the art without departing from the spirit and the scope of the following claims.

I claim:

1. A method of prospectively planning utilization of a multiplicity of related resources using a computer having a memory, including the steps of:
   identifying some of said resources as being primary, and other resources as being secondary;
   establishing temporal relationships between at least some of said resources;
   creating a data base of information about at least one of said resources, at least some of which information is independent of said temporal relationships between resources;
   prospectively scheduling utilization of at least some of said primary resources and at least some of said secondary resources;
   displaying, in graphical fashion, the prospectively scheduled utilization of at least some of said resources;
   determining whether any of said scheduled utilizations of one of said resources is incompatible with any of the information in said data base; and
   communicating, by means of conflict indicia, the existence of any said incompatible scheduled utilizations.

2. The method of claim 1 wherein said display is a transient optical display and wherein said communication of at least one of said conflict indicia is accomplished by having same appear on said display.

3. The method of claim 2 further comprising the step of displaying status indicia.

4. The method of claim 2 wherein at least two different types of conflict indicia are displayed.

5. The method of claim 4 wherein one of said types of conflict indicia identifies a temporal conflict and another conflict indicia identifies an impermissible use as determined by a search of said data base.

6. The method of claim 4 wherein at least some of said conflict indicia identify the type of conflict involved.

7. The method of claim 2 further comprising the steps of displaying utilization information about at least some primary resources;
   displaying utilization information about at least some of said secondary resources; and
   displaying a relationship between at least one of said primary resources to at least one of said secondary resources.

8. The method of claim 2 wherein there is displayed simultaneously at least one primary resource and at least one secondary resource.

9. The method of claim 2 wherein the display of information is dynamic in that it reflects status information in real time.

10. The method of claim 2 wherein at least one of said conflict indicia identifies a real conflict and at least one other of said conflict indicia identifies an apparent conflict.

11. The method of claim 2 wherein said data base can be interrogated to cause a display of information about at least one of said resources.

12. The method of claim 1 further comprising the steps of:
    obtaining information representing actual utilization of at least one of said resources at a point in time subsequent to the first scheduled utilization of said resource;
    determining whether said actual utilization is incompatible with any of said temporal relationships or with any information stored in said data base; and
    communicating, by means of conflict indicia, the existence of any such incompatible utilizations.

13. The method of claim 1 further comprising the step of determining whether any of said scheduled utilizations is incompatible with any of said temporal relationships.

14. The method of prospectively planning utilization of a multiplicity of related resources using a computer having a memory, including the steps of:
    creating a data base of information about at least some of said resources, at least some of which data is independent of temporal relationships between resources;
    including in said data base permissible and impermissible uses of at least some of said resources;
    prospectively scheduling utilization of at least some of said resources;
    displaying, in graphical fashion, the prospectively scheduled utilization of at least some of said resources;
    searching said data base to determine if any of said scheduled utilizations constitutes an impermissible use; and
    communicating, by means of conflict indicia, said impermissible scheduled utilizations.

15. The method of claim 1 or 14 wherein communication of at least some of said conflict indicia is by means of sound.

16. The method of claim 1 or 14 wherein communication of at least some of said conflict indicia is by means of light, radio waves or other electromagnetic radiation.

17. The method of claim 14 wherein said display is a transient optical display and wherein said communication of at least one of said conflict indicia is accomplished by having same appear on said display.

18. The method of claim 17 wherein said prospectively scheduled utilization is reflected on said display in the form of scheduling indicia.

19. The method of claim 18 further comprising the steps of:
    obtaining information representing actual utilization of at least one of said resources at a point in time subsequent to the first scheduled utilization of said resource;

communicating said actual utilization information by having same appear on said display in the form of status indicia.

20. The method of claim 19 further comprising the steps of:

determining whether said actual utilization is inconsistent with any prior scheduled utilizations of any resource;

rescheduling at least one of said inconsistent previously scheduled utilizations.

21. The method of claim 19 further comprising the step of recording said actual utilizations.

22. The method of claim 14 further comprising the step of communicating at least two different types of conflict indicia.

23. The method of claim 22 wherein one of said conflict indicia identifies a temporal conflict and another of said conflict indicia identifies an impermissible use as determined by a search of said data base.

24. The method of claim 14 wherein said data base is comprised of a permanent or semi-permanent data base and a transitory data base.

25. A system for prospectively planning utilization of a multiplicity of resources, at least some of which are interrelated, comprising:

a computer having a memory;

a data base stored in said memory containing information about at least some of said resources, at least some of which information is independent of temporal relationships between resources;

a set designated as primary resources and a set designated as secondary resources;

scheduling means for prospectively scheduling utilization of at least some of said primary resources as a function of time;

display means for displaying in graphical form, the prospectively scheduled utilization of at least some of said resources;

means for comparing at least one of said scheduled utilizations with at least one other scheduled utilization or with information in said data base, to detect incompatibilities; and means for communicating, by use of conflict indicia, the existence of detected incompatibilities.

26. The system of claim 25 wherein said display means are characterized by being transient.

27. The system of claim 26 wherein at least some of said scheduling information is made to appear in textual form on said display.

28. The system of claim 27 wherein at least some of said conflict indicia are made to appear on said display.

29. The system of claim 28 wherein said scheduling information reflects planned utilization of at least some of said primary resources as a function of time.

30. The system of claim 29 wherein at least some of said scheduling information incorporates information about utilization of at least some of said secondary resources.

31. The system of claim 28 wherein at least some of said conflict indicia appear on said graphical display.

32. The system of claim 25 wherein at least some of said conflict indicia appear on said graphical display.

33. The system of claim 25 wherein at least two different kinds of conflict indicia are employed to communicate the existence of at least two different kinds of incompatibilities.

34. The system of claim 33 wherein at least one of said conflict indicia identifies a temporal incompatibility and at least one other conflict indicia identifies an incompatibility as determined by a search of said data base.

35. A system for prospectively scheduling, periodic monitoring and managing utilization of a plurality of resources, at least some of which are interrelated, comprising:

a computer having a memory;

a data base stored in said memory, containing information about at least some of said resources; at least some of which information is independent of temporal relationships between resources;

a set designated as primary resources and a set designated as secondary resources;

scheduling means for prospectively scheduling utilization of at least some of said primary resources as a function of time;

display means for displaying in graphical form, the prospectively scheduled utilization of at least some of said resources;

means for communicating at least some of said prospectively scheduled utilization information through use of graphically displayed scheduling indicia;

means for comparing at least one of said scheduled utilizations with at least one other scheduled utilization or with information in said data base to detect incompatibilities;

means for communicating, by use of conflict indicia, the existence of detected incompatibilities;

means for collecting information about actual utilization of at least one of said primary resources subsequent to the first scheduled use of a resource; and means for modifying at least one of said scheduled utilizations to reflect variances between said actual utilization and said prospectively scheduled utilization.

36. The system of claim 35 further comprising means for inputting the actual status of utilization of at least one of said primary resources at a point in time subsequent to the initial planned utilization of at least one of said primary resources.

37. The system of claim 36 further comprising means for collecting information about actual utilization of at least one of said primary resources at a point in time subsequent to the first prospectively scheduled utilization thereof and means for communicating said actual utilization information by use of status indicia.

38. The system of claim 37 further comprising means for comparing said actual utilization of at least one of said primary resources with the prospectively scheduled utilization of said resource and means for communicating, through use of status indicia, the results of said comparison.

39. The system of claim 37 wherein said means for collecting information about actual utilization of resources includes real time clock means.

40. The system of claim 37 wherein said display means includes means for displaying at least one of said conflict indicia or said status indicia.

41. The system of claim 37 further comprising means for dynamically displaying, by use of said status indicia, the status of utilization of at least one of said resources in real time.

42. The system of claim 36 wherein said means for inputting said actual utilization status of resources includes real time clock means.

43. The system of claim 36 further comprising means for recording the time of said inputting of said actual status utilization data.

44. The system of claim 36 further comprising means for recording the time of said actual status utilization.

45. The system of claim 25 or claim 35 wherein said data base is comprised of a semi-permanent data base and a transitory data base.

46. The system of claim 35 wherein said means for collecting said actual utilization information includes real-time clock means.

47. The system of claim 46, 41, or 39 wherein said real time clock means is made to appear concurrently with said graphical display of the prospectively scheduled utilization of at least some of said resources.

48. The system of claim 35 further comprising means for detecting modification-caused incompatible utilizations and communicating said detected modification-caused incompatibilities by use of conflict indicia.

49. The system of claim 48 wherein said display means includes means for displaying at least one of said conflict indicia or said status indicia.

50. The system of claim 35 wherein said display means are characterized by being transient in nature.

51. The system of claim 35 wherein said modifying means includes means for automatically altering at least one of said scheduled utilizations in response to detection of at least one modification-caused incompatibility.

52. The system of claim 35 wherein at least some of said actual utilization information appears on said graphical display.

53. The system of claim 32, 31 or 52 wherein said graphical display is made to appear concurrently with a textual display of information about utilization of at least some of said primary or secondary resources.

54. The system of claim 26 wherein information stored in said data base about at least one of said resources can be accessed and made to appear on said display.

55. The system of claim 35 wherein at least one of said conflict indicia is communicated by graphical display thereof.

56. The system of claim 26 or 55 further comprising
means for displaying utilization information about at least some of said primary resources;
means for displaying utilization information about at least some of said secondary resources; and
means for displaying a relationship between at least one of said primary resources and at least one of said secondary resources.

57. The system of claim 26 or 55 further comprising means for simultaneously displaying information about at least one primary resource and at least one secondary resource.

58. The system of claim 26 or 55 further comprising means for dynamically displaying on said transient display, status information about the utilization of at least some of said resources in real time.

59. The system of claim 26 or 55 wherein at least one of said conflict indicia identifies a real conflict and at least one other conflict indicia identifies an apparent conflict.

60. The system of claim 26 or 55 further comprising means for interrogating said data base to cause a display of information about one of said resources.

61. The system of claims 26 and 55 wherein at least two different kinds of incompatibilities can be detected and wherein at least some of said conflict indicia identify the nature of the incompatibility associated therewith.

* * * * *

UNITED STATES PATENT AND TRADEMARK OFFICE
CERTIFICATE OF CORRECTION

PATENT NO. : 4,937,743
DATED : June 26, 1990
INVENTOR(S) : WILLIAM R. RASSMAN ET AL.  Page 1 of 4

It is certified that error appears in the above-identified patent and that said Letters Patent is hereby corrected as shown below:

SHEET 9 OF 9

Figure 9, "Pulmonary Emphysemia" should read
--Pulmonary Emphysema--.

COLUMN 2

Line 31, "such." should read --such--.

COLUMN 4

Line 7, "an" should read --a--.
Line 57, "semi permanent" should read --semi-permanent--.

COLUMN 5

Line 12, "on audible" should read --an audible--.
Line 13, "schedule" should read --scheduled--.

COLUMN 6

Line 9, ""Status indicia."" should read
--"status indicia."--.
Line 45, "anaesthesiologist's." should read
--anaesthesiologists.--.

COLUMN 7

Line 41, ""construction" "sabatical"" should read
--"construction", "sabbatical"--.

UNITED STATES PATENT AND TRADEMARK OFFICE
CERTIFICATE OF CORRECTION

PATENT NO. : 4,937,743
DATED : June 26, 1990
INVENTOR(S) : WILLIAM R. RASSMAN ET AL.    Page 2 of 4

It is certified that error appears in the above-identified patent and that said Letters Patent is hereby corrected as shown below:

COLUMN 8

Line 34, "resource s" should read --resource's--.
    Line 37, "menu driven." should read --menu-driven.--.
    Line 68, "the the" should read --the--.

COLUMN 9

Line 7, "9:00" should read --09:00--.
    Line 8, "09:,30." should read --09:30.--.
    Line 64, "two dimensional" should read --two-dimensional--.

COLUMN 11

Line 36, "contemporoue-" should read --contemporane---.

UNITED STATES PATENT AND TRADEMARK OFFICE
CERTIFICATE OF CORRECTION

PATENT NO. : 4,937,743

DATED : June 26, 1990

INVENTOR(S) : WILLIAM R. RASSMAN ET AL.   Page 3 of 4

It is certified that error appears in the above-identified patent and that said Letters Patent is hereby corrected as shown below:

<u>COLUMN 11</u>

Line 48, "involved to" should read
--involved.
   The system can also be made to take certain actions automatically. For example, if a piece of equipment must be warmed up for a predetermined period of time before use, the method of the instant invention would encompass having the system energize that piece of equipment when a particular milestone in the procedure has been completed. Similarly, in an industrial setting, the system could automatically cut purchase orders or open molds when certain predetermined milestones are reached.
   The method of this invention also contemplates a rule based system wherein the detection of certain conflict indicia would cause automatic rescheduling of some resources. To illustrate, assume that in FIG. 1, there must be 15 minutes between completing Case abc and beginning Case def. If a signal has not been sent by 8:50 that Case abc is over, a rule could be established that would automatically reschedule Case def to begin at 9:15. The rule could also require checking the schedules of all the resources involved in Case def before rescheduling.
   If, upon checking those Case def-related schedules no new conflicts are detected, the rescheduling would be done and notice of the change communicated automatically to the people affected. This could be done, for example, by having the system call the office of the surgeon scheduled to do Case def and, by use of a voice synthesizer, report the new schedule.
   If the rescheduling of Case def is found to provoke other conflicts, the system could be designed so as not to do the rescheduling, but instead merely to give notice of the first conflict. That notice could be by means of a visual display, by the sounding of a distinctive note or the like. Another possibility would be to have the system try to--.

UNITED STATES PATENT AND TRADEMARK OFFICE
CERTIFICATE OF CORRECTION

PATENT NO. : 4,937,743

DATED : June 26, 1990

INVENTOR(S) : WILLIAM R. RASSMAN ET AL.      Page 4 of 4

It is certified that error appears in the above-identified patent and that said Letters Patent is hereby corrected as shown below:

COLUMN 12

Lines 14-48, lines 14 to 48 should be deleted.

COLUMN 14

Line 19, "Phase of" should read --Phase 1 of--.
　　　Line 52, "pop up" should read --pop-up--.
　　　Line 55, "pop up" should read --pop-up--.

COLUMN 15

Line 26, "I claim:" should read --We claim:--.

COLUMN 17

Line 2, "resource;" should read --resource; and--.
　　　Line 10, "resource;" should read --resource; and--.
　　　Line 52, "claim 27" should read --claim 26--.

Signed and Sealed this

Thirty-first Day of March, 1992

Attest:

HARRY F. MANBECK, JR.

Attesting Officer　　　Commissioner of Patents and Trademarks